US012629033B2

(12) United States Patent
Goth et al.

(10) Patent No.: US 12,629,033 B2
(45) Date of Patent: May 19, 2026

(54) MULTIMODAL PROBES FOR TISSUE INTERROGATION

(71) Applicant: SpectraWAVE, Inc., Bedford, MA (US)

(72) Inventors: Will Goth, Waltham, MA (US); Tsung-Han Tsai, Newton, MA (US); Eman Namati, Concord, MA (US); Damon T. DePaoli, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/710,718

(22) PCT Filed: Nov. 18, 2022

(86) PCT No.: PCT/US2022/050460
§ 371 (c)(1),
(2) Date: May 16, 2024

(87) PCT Pub. No.: WO2023/091701
PCT Pub. Date: May 25, 2023

(65) Prior Publication Data
US 2025/0017471 A1     Jan. 16, 2025

Related U.S. Application Data

(60) Provisional application No. 63/281,383, filed on Nov. 19, 2021.

(51) Int. Cl.
*A61B 5/00*     (2006.01)
*A61B 90/00*     (2016.01)

(52) U.S. Cl.
CPC .......... *A61B 5/0084* (2013.01); *A61B 5/0066* (2013.01); *A61B 2090/3966* (2016.02); *A61B 2562/0233* (2013.01)

(58) Field of Classification Search
CPC ..................................................... A61B 5/0084
See application file for complete search history.

(56) References Cited

U.S. PATENT DOCUMENTS

2001/0055462 A1     12/2001     Seibel
2012/0101374 A1     4/2012     Tearney et al.
(Continued)

FOREIGN PATENT DOCUMENTS

WO     WO-2023/091701 A1     5/2023

OTHER PUBLICATIONS

International Search Report for PCT/US2022/050460, 4 pages, mailing date Mar. 17, 2023.
(Continued)

*Primary Examiner* — Joseph M Santos Rodriguez

(57) ABSTRACT
Aspects of the disclosure relate to the use of an optical detection scheme enabling multiple imaging sub-systems concurrently optimized for retrieving multiple characterization modalities. The feature described is an offset illumination and detection arrangement for a multimodal imaging probe. The imaging probe comprises multiple waveguides disposed within a torque-transfer coil, distally terminating at longitudinally separated positions. A first waveguide may have focusing optics for focused illumination and/or detection. Any number of other waveguides may be deployed for illumination and/or detection having no focusing optics. The disclosure enables high-fidelity multimodal imaging systems.

14 Claims, 8 Drawing Sheets

(56)         References Cited

U.S. PATENT DOCUMENTS

| | | |
|---|---|---|
| 2013/0107274 A1 | 5/2013 | Vertikov et al. |
| 2015/0272442 A1 | 10/2015 | Motafakker-Fard et al. |
| 2017/0238807 A9 | 8/2017 | Vertikov |

OTHER PUBLICATIONS

Muller, J. and Madder, R., OCT-NIRS Imaging for Detection of Coronary Plaque Structure and Vulnerability, Frontiers in Cardiovascular Medicine, 7(90):1-10 (2020).
Written Opinion for PCT/US2022/050460, 7 pages, mailing date Mar. 17, 2023.

MULTIMODAL PROBES FOR TISSUE INTERROGATION

PRIORITY APPLICATION

This application claims the benefit of U.S. Provisional Patent Application No. 63/281,383, filed on Nov. 19, 2021, the disclosure of which is hereby incorporated by reference herein in its entirety.

TECHNICAL FIELD

This disclosure relates generally to methods of detecting and characterizing objects within bodily lumens using optical waveguides.

BACKGROUND

In many applications, multiple sample characterization modalities are used to characterize a sample. Multimodal characterization can be performed using different forms of electromagnetic (e.g., optical) radiation from a single waveguide (e.g., optical fiber) or from a plurality of waveguides. It can be difficult to optimize the illumination and detection design for a plurality of optical modalities. Accordingly, information (e.g., image) quality can often suffer for at least one of the plurality of modalities in a multimodal system.

SUMMARY

Coronary artery disease (CAD) is the leading cause of death in the United States and the world, with over 1 million percutaneous coronary intervention (PCI) procedures performed per year to combat CAD. Unfortunately, 1 in 5 patients undergoing PCI procedure will suffer a major adverse cardiovascular event (MACE) within 2 years from either failure at the PCI site or de novo coronary lesion formation from rupture of high-risk vulnerable plaques. The ability to both optimize treatment of PCI and identify patients and plaques at high risk of future rupture would allow physicians to manage and prevent the major causes of future MACE. In order to optimize such procedures, intravascular characterization may be performed to examine the arterial walls, using small diameter probes (e.g., less than 500 µm outer diameter probes, e.g., less than 1000 µm outer diameter probes). Intravascular characterization can provide information to the physician and aid in clinical decision making. Intravascular characterization systems that can utilize a plurality of modalities (e.g., using the same intravascular probe) are therefore of greater benefit to a clinician, as they can provide more information to make decisions. Furthermore, one modality (e.g., an interferometric imaging modality) may improve one unique clinical endpoint (e.g., PCI optimization) while another modality (e.g., spectroscopy) may serve another clinical purpose (e.g., detection of vulnerable plaques).

Intraluminal characterization (e.g., of the arterial wall) can be performed using electromagnetic radiation. In some instances, characterization can be improved if more than one method of characterization is performed (e.g., multimodal characterization). However, there exist challenges in multimodal characterization. For instance, some modalities require singlemode waveguides (e.g., singlemode fiber optics) while some require multimode waveguides (e.g., multimode fiber optics). In some cases, a combination my even be desirable, for example depending on which modalities are being used. Furthermore, one modality may require focused illumination or detection, or both, while another modality may simply require maximizing illumination or detection area. In some cases, the amount of light detected should be minimized/maximized or optimally controlled to utilize a detector's dynamic range. Some modalities require a predictable phase change (e.g., 180°) while some modalities are phase change agnostic. Some modalities depend on coherence preservation (e.g., an interferometric imaging system), while other modalities do not (e.g., spectroscopy). Some modalities create contrast using specular reflections, while other modalities can produce contrast using diffuse reflections (e.g., diffuse reflectance spectroscopy). For some modalities, it is desirable to separate, or control the distance, and or position, between the illumination and the detection areas (e.g., to control depth of sensing or to minimize specular reflection). Some modalities it may be advantageous to control the angle of incidence of the radiation on a sample (e.g., to reduce surface reflections, e.g., surface reflections from a protective probe sheath, e.g., surface reflections from a sample).

One example system includes an imaging modality and a spectroscopy modality. The imaging modality (e.g., an interferometric imaging system) used for structural sample interrogation, where focused illumination and detection may be desirable, such as to provide high resolution information. The spectroscopy modality (e.g., a NIRS system) used for molecular (e.g., chemical) sample interrogation, may favorably also use focused illumination when it may be undesirable to use focused detection, as that may minimize collection efficiency. Therefore, to perform multimodal characterization with such an imaging modality and such a spectroscopy modality, each modality's performance may be optimized using a unique multimodal probe. Ultimately, many factors must be considered when designing multimodal characterization probes and the current disclosure is based on this recognition.

In the case of arterial wall characterization, an important challenge comes from the size constraint of designing a probe that can fit within the vessel to characterize it. As such, many designs have been deployed in order to address this issue deploying complicated distal probe optics and specialized sheaths containing fiber optics. The present disclosure provides, inter alia, a simplified and performance-optimized probe for multimodal characterization resulting from unanticipated observations and subsequent experimentation and analysis. The present disclosure also provides waveguide arrangements with improved manufacturability thereby reducing cost of manufacture.

According to some embodiments, a multimodal system may comprise of a multimodal probe for intraluminal characterization, the multimodal probe having a proximal end and a distal end, where the distal end may be optically coupled to a sample. A multimodal probe may be disposed such that electromagnetic radiation (e.g., light) transmitted to the sample travels through a first waveguide (e.g., a singlemode fiber) and backscattered electromagnetic radiation, received after interaction with the sample (e.g., a coronary artery), may travel through more than one waveguide (e.g., a singlemode fiber and a multimode fiber). In some embodiments of the present disclosure, a multimodal probe may contain at least two optical waveguides within a torque-transfer coil (e.g., a drive shaft) used to rotate the distal portion of the probe in a circumferential manner (e.g., to image the interior of a bodily lumen (e.g., artery)).

In some embodiments, a single waveguide may be used for illumination and detection while either the same waveguide, or another, is used for detection. In some embodiments, a distal port of the waveguides (e.g., where electromagnetic radiation is optically transmitted to the sample) are optimally offset longitudinally, or circumferentially, such as to optimize source detector separation for optical measurements (e.g., scattering measurements, e.g., anisotropy measurements, e.g., absorption measurements).

A multimodal probe may comprise distal optics that are optimized for each modality in a multimodal characterization system. In some embodiments, an illumination waveguide is optically coupled to a distal focusing optic (e.g., to focus light on the sample), such as to optimize resolution of a characterization modality (. In some embodiments, a collection waveguide is not optically coupled to distal focusing optics, such as to maximize collected light for a characterization modality.

In some embodiments, a singlemode waveguide may be used to transmit singlemode light to and from the sample for an imaging modality (e.g., optical coherence tomography (OCT), e.g., confocal microscopy). In some embodiments, a multimode waveguide may be used to transmit multimode light to and from the sample for reflectance-intensity modality (e.g., diffuse spectroscopy, fluorescence spectroscopy, Raman spectroscopy).

In some embodiments, the source to detector offset between the illumination and the collection waveguide can optimize the collection of diffusely reflected light (e.g., relative to specularly reflected light), (e.g., to interrogate the sub-surface of the sample.) In some embodiments, the central-axis of an illuminating beam, for a given characterization modality, may be deflected (e.g., reflected) towards the sample (e.g., away from the characterization probe's central axis). In some embodiments, the angle of incidence for radiation impinging a sample from a first waveguide (e.g., for illumination) is controlled relative to the angle of the center axis of another waveguide's collection area. In some embodiments, the center axis of an impinging beam in optical transmission with one waveguide (e.g., an illumination waveguide) is longitudinally offset from the center axis of an impinging beam in optical transmission with another waveguide (e.g., a collection waveguide).

In some embodiments, each modality may use a unique light source, multiple light sources, or may use the same light source. In some embodiments, a light source may be use a narrow wavelength band, a broad wavelength band and/or may be wavelength-swept or wavelength-tunable. In some embodiments, the duty cycle of multiple light sources may be interleaved in time to allow multimodal characterization in a single pullback.

In some embodiments, a first characterization modality may be an imaging modality, for example optical coherence tomography (OCT). A second characterization modality may be a spectroscopy modality, for example near-infrared spectroscopy (NIRS). In some embodiments, a multimodal probe is a catheter, for example a cardiac catheter that can be used to rapidly characterize lumens (e.g., arteries) of a patient, in a multimodal manner.

In some embodiments, a probe for characterizing bodily lumens is provided. The probe may include a first waveguide and a second waveguide, each extending to a distal end of the probe. A first beam redirector and/or a focusing optic (e.g., a combined focusing optic and beam redirector) may be disposed in an optical path of the first waveguide such that a first beam transmitted by the first waveguide can be focused towards a wall of a lumen (e.g., a bodily lumen). A second beam redirector may be disposed in an optical path of the second waveguide such that a second beam transmitted by second waveguide can be directed towards the wall (e.g., without a focusing optic). The first beam redirector, the focusing optic, and the second beam redirector may be arranged such that, when provided in the lumen, a center of the first beam points at a position on the wall that is more distal than a center of the second beam. In some embodiments, the first waveguide and the second waveguide may share a single beam redirector after a focusing optic disposed in the optical path of the first waveguide.

In some embodiments, the first waveguide is constructed to detect signal for a first characterization modality and the second waveguide is constructed for a second characterization modality and the first characterization modality is an interferometric imaging modality (e.g., OCT).

In some embodiments, the first beam redirector is positioned more distal than the second beam redirector. In some embodiments, there is no focusing optic disposed in the optical path between the second waveguide and the wall of the lumen. In some embodiments, the first and second waveguides are disposed within a torque transfer coil. In some embodiments, the first beam redirector and the focusing optic are physically connected with the first waveguide and the second beam redirector is physically connected with the second waveguide.

In some embodiments, the first beam redirector or the second beam redirector is an angled fiber optic. In some embodiments, the focusing optic is an ball lens (e.g., an integrated ball lens). In some embodiments, the focusing optic is a gradient index lens. In some embodiments, the first beam redirector and the focusing optic are each (e.g., are together) a curved mirror surface. In some embodiments, an injection molded piece comprises the first beam redirector, the second beam redirector and the focusing optic. In some embodiments, a 3D printed piece comprises the first beam redirector, the second beam redirector and the focusing optic.

In some embodiments, a protective encasement is placed around the distal end of the probe. In some embodiments, the protective encasement comprises an optically transparent window. In some embodiments, the protective encasement comprises a radiopaque substance.

In some embodiments, the probe comprises a spectroscopic modality subsystem (e.g., NIRS, autofluoresence, fluorescence, Raman) optically connected to the second waveguide to detect light received through the second waveguide. In some embodiments, the probe comprises a characterization modality subsystem optically connected to the first waveguide such that a reflectance intensity is detected by the first waveguide. In some embodiments, the probe comprises an interferrometric modality subsystem (e.g., OCT or OFDI) optically connected to the first waveguide (e.g., wherein the first waveguide is an illumination waveguide and a collection waveguide for the interferrometric modality). In some embodiments, the probe comprises an intensity modality subsystem (e.g., spectroscopy, NIRS, fluorescence, Raman) optically connected to the second waveguide (e.g., wherein the second waveguide is an illumination waveguide and/or a collection waveguide for the intensity modality).

In some embodiments, the second waveguide is optically connected to a light source to illuminate the sample. In some embodiments, the probe comprises at least one additional waveguide. In some embodiments, the second waveguide is not associated with (e.g., optically connected to) any focusing optic at the distal end of the probe. In some embodiments, the first redirector, the focusing optic, and the second redirector are disposed such that the beam from the first waveguide and the beam from the second waveguide do not circumferentially overlap. In some embodiments, the probe is rotatable.

In some embodiments, a probe for characterizing bodily lumens is provided. The probe may include a first waveguide and a second waveguide. A first beam redirector and/or a focusing optic may be disposed in an optical path of the first waveguide. A second beam redirector may be disposed in an optical path of the second waveguide. In some embodiments, the first beam redirector and the focusing optic are arranged to focus a center of a beam from the first waveguide at a first position (e.g., on a lumen wall) and the second beam redirector is arranged to provide a center of beam from the second waveguide at a second position. The first position may be offset (e.g., radially offset) by a distance from the second position.

In some embodiments, the first position is distal to the second position (e.g., along a wall of a bodily lumen). In some embodiments, the first redirector, the focusing optic, and the second redirector are disposed such that the beam from the first waveguide and the beam from the second waveguide do not circumferentially overlap. In some embodiments, the second waveguide is not associated with (e.g., optically connected to) any focusing optic at the distal end of the probe.

In some embodiments, the probe comprises an interferrometric modality subsystem (e.g., OCT or OFDI) optically connected to the first waveguide (e.g., wherein the first waveguide is an illumination waveguide and a collection waveguide for the interferrometric modality). In some embodiments, the probe comprises an intensity modality subsystem (e.g., spectroscopy, NIRS, fluorescence, Raman) optically connected to the second waveguide (e.g., wherein the second waveguide is an illumination waveguide and/or a collection waveguide for the intensity modality).

In some embodiments, the first beam redirector and the focusing optic are arranged to focus the beam from the first waveguide in a radial direction and/or wherein the second beam redirector is arranged to direct the beam from the second waveguide in a (e.g., the) radial direction.

A probe may be included in an (e.g., intravascular) imaging catheter. An outer diameter of the catheter may be less than 1 mm over a lumen-insertable length of the catheter. In some embodiments, the imaging catheter is part of a multimodal (e.g., intravascular) imaging system. In some embodiments, a probe is an air-filled probe. In some embodiments, a catheter is an air-filled catheter. In some embodiments, a probe is in optical communication with a rotatable combiner. A rotatable combiner may be optically coupled to a fiber optic rotary junction (FORJ), for example a double clad FORJ. A rotatable combiner may combine electromagnetic radiation from one or more illumination optical channels and/or one or more waveguides, for example for transmission over a FORJ. A FORJ may be optically coupled to a probe via a rotatable combiner.

Other features and advantages of the disclosure will be apparent from the following detailed description, and from the claims. Unless otherwise clear from context, any two or more of the features described in this specification, including in this summary section, may be combined to form implementations not specifically explicitly described in this specification.

BRIEF DESCRIPTION OF THE DRAWINGS

Drawings are presented herein for illustration purposes, not for limitation. The foregoing and other objects, aspects, features, and advantages of the disclosure will become more apparent and may be better understood by referring to the following description taken in conjunction with the accompanying drawings, in which.

DEFINITIONS

Figure 1:
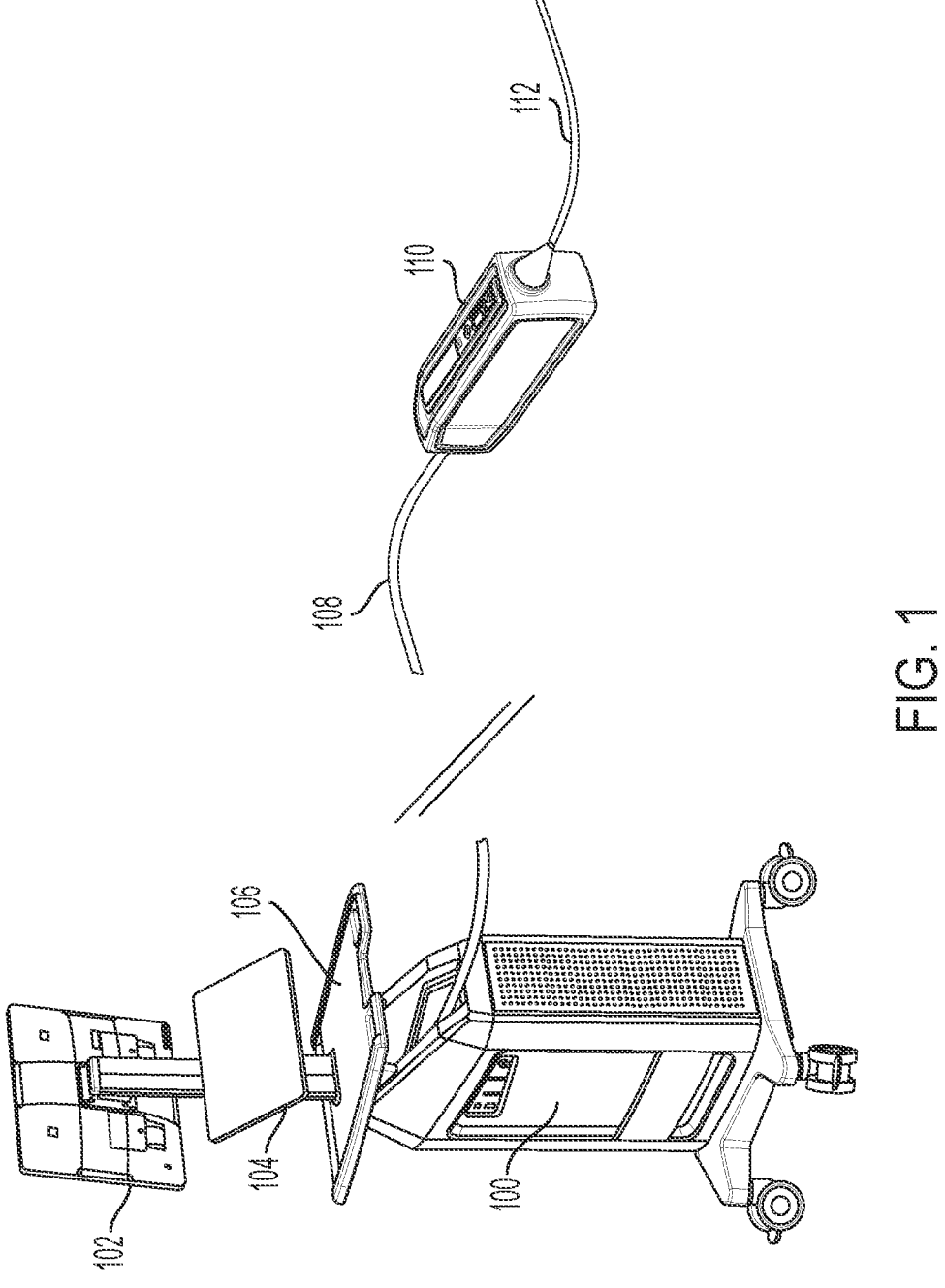
FIG. 1 illustrates a multimodal imaging system in accordance with illustrative embodiments of the present disclosure.

In order for the present disclosure to be more readily understood, certain terms used herein are defined below. Additional definitions for the following terms and other terms may be set forth throughout the specification. In this application, unless otherwise clear from context or otherwise explicitly stated, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Probe": as used herein, a "probe" refers to a device for transmitting information (e.g., signal, e.g., electromagnetic radiation) from a proximal end (e.g., the operator end) and a distal end (e.g., the sample end). As used herein, a "longitudinal" direction refers to a direction along a long axis of the probe, a "azimuthal" or "circumferential" direction refers to a direction along a circumference of the probe, waveguide or other essentially cylindrical structure, and a "Radial" direction refers to a direction along a radius of the probe, waveguide, or other essentially cylindrical structures.

"Light source": as used herein, a "light source" refers to a source that provides (e.g., emits) light. Light is electromagnetic radiation (EMR) (e.g., photons). As used herein, light may have a frequency (wavelength) in a visible spectrum or not. A light source may emit one or more of visible light, near-infrared light, infrared light, long wavelength infrared light, ultraviolet light, deep ultraviolet light, and extreme ultraviolet light. In some embodiments, a light source may emit terahertz radiation. A light source may emit x-rays, microwaves, or radio waves. A light source may be, but is not necessarily, a laser. A light source may be, for example, a light source with reduced temporal coherence such as a source comprising a light emitting diode (LED) or a superluminescent diode (SLD). A light source may be a swept source, a tunable source or a narrowband source. In certain embodiments, a light source is a swept-source laser. In certain embodiments, a light source is a broadband source.

"Image": as used herein, the term "image," for example, as in a two- or three-dimensional image of tissue (or other sample), includes any visual representation, such as a photo, a video frame, streaming video, as well as any electronic, digital, or mathematical analogue of a photo, video frame, or streaming video. Any system or apparatus described herein, in certain embodiments, includes a display for displaying an image or any other result produced by a processor. Any method described herein, in certain embodiments, includes a step of displaying an image or any other result produced by the method. Any system or apparatus described herein, in certain embodiments, outputs an image to a remote receiving device [e.g., a cloud server, a remote monitor, or a hospital information system (e.g., a picture archiving and communication system (PACS))]. In some embodiments, an image is produced using a fluorescence imaging system, a spectroscopic imaging system, a luminescence imaging system, and/or a reflectance imaging system. In certain embodiments, a tomographic image and a spectroscopic image are co-registered to form a composite image. In some embodiments, an image is a two-dimensional (2D) image. In some embodiments, an image is a three-dimensional (3D) image. In some embodiments, an image is a reconstructed image. An image (e.g., a 3D image) may be a single image or a set of images. An imaging technique (e.g., using light provided by a light source) may produce one or more images.

"Sample": As used herein, "sample" refers to matter to be characterized. Generally, any material, mixture, substance, or capable of characterization by a light can be used as a sample. A sample may comprise one or more materials. A sample may be gaseous, fluid, or solid. A sample may be, for example, a gel (e.g., a hydrogel), an elastomer, or a composite. A sample may be a biological sample. For example, a sample may be an organ or biological structure (e.g., tissue) or portion thereof. A sample may be an in vivo organ or in vivo tissue. For example, a sample may be an in vivo artery or portion thereof. A sample may comprise one or more features of interest. For example, a feature of interest may be, for example, arterial plaque (e.g., a vulnerable plaque, for example having a fibrous cap).

"Spectroscopy": as used herein, "spectroscopy" refers to any form of characterization of a sample with a light source with a specific wavelength range. A light source may have a narrowband (e.g., less than 2 nm) wavelength range (e.g., 1210.01-1210.02 nm, e.g., 1210 nm-1212 nm), a broadband wavelength range (e.g., 1160 nm-1280 nm), or more than one non-contiguous bands of wavelengths (e.g., 1205 nm-1215 nm and 1260 nm-1360 nm). For example, "visible spectroscopy" may refer to characterizing (e.g., imaging) a sample at a visible wavelength (e.g., 550 nm). As another example, "near infrared spectroscopy/NIRS" may refer to characterizing (e.g., imaging) a sample at a NIRS wavelength (e.g., 1210 nm). In some embodiments, scanning any source over any area of a sample can produce an image, and, this process may still be termed spectroscopy as the image pertains to the absorption and scattering characteristics of the sample in a specific wavelength range.

"Optical" is not limited to referring to visible light. For example, an optical channel may be constructed to transmit light having a frequency (wavelength) outside of the visible spectrum, such as infrared or ultraviolet light. Similarly, "optical detection," "optical modality," and other similar terms can utilize light (electromagnetic radiation) outside of the visible spectrum, such as infrared or ultraviolet light. Two components that are "optically connected" may be directly optically connected or have one or more additional optical components (e.g., waveguide(s), lens(es), beam splitter(s), multiplexer(s)) and/or free space disposed therebetween along an optical path.

"Specular reflections": as used herein, specular reflections refer to mirror-like reflections, that is, light that is reflected from the surface of a sample at the same angle as the incident ray, but on the opposite side of a plane normal to the surface. In practical optical characterization systems, the impinging light may be a perfectly collimated beam, a focusing beam, or a beam having a finite beam divergence. In the practical case therefore, specular reflection refers to the axis of the beam.

"Diffuse reflections": as used herein, diffuse reflections refer to light that emerges from the surface of a sample in a range of directions after having been scattered. Most surfaces exhibit a combination of diffuse and specular reflectance.

DETAILED DESCRIPTION OF CERTAIN EMBODIMENTS

Intraluminal characterization generally comprises rapidly rotating a probe to characterize the inner circumference of an internal object, as is performed in typical catheter-based intravascular characterization systems. Such characterization probes generally consist of an optical waveguide that transmits and receives light between the optical system and the sample.

Characterization probes can be designed to optimize a single characterization modality, or multiple. For example, a characterization probe may be designed to characterize structural properties of a sample (e.g., by imaging, for example with OCT). A characterization probe may also be designed to characterize molecular properties of a sample (e.g., by performing spectroscopy, for example with NIRS) A characterization probe may be designed to characterize more than one property of a sample using multiple characterization modalities (e.g., OCT imaging and NIRS). Such probes require careful optimization to provide high sensitivity and fidelity characterization with both modalities.

Interferometric imaging, such as OCT, is optimally performed using focused light. Diffuse spectroscopy, on the other hand, can be optimized in many ways. For instance, an optimization may include an optical arrangement that favors detection of light that has interacted with subsurface molecules (e.g., diffusely reflectance) rather than light that has interacted with only the surface (e.g., specular reflections). Another optimization may include an optical arrangement that favors deep tissue sensing (e.g., by controlling the source to detector distance). Another optimization may include whether or not to use focused illumination or detection based on signal collection efficiency. Finally, in the context of intraluminal characterization in a medical context, all these optimizations need to be performed under considerable probe design constraints (e.g., size, robustness, manufacturability, cost).

The current disclosure provides, among other things, an optimal optical arrangement to perform imaging and spectroscopy. For example, in certain embodiments, performance losses are minimized for structural imaging, thereby allowing state-of-the-art interferometric sensitivity (e.g., greater than 90 dB, greater than 100 dB, or greater than 110 dB) while also maximizing the ratio of wanted (e.g., diffuse light) versus unwanted (e.g., specular) signal collection for spectroscopy. Furthermore, in certain embodiments, manufacturability is maximized by reducing complicated optics on the probe, minimizing the cost-of-goods for the probe. Moreover, certain embodiments of the present disclosure permit optimization (e.g., minimization) of the size of the probe.

Previous spectroscopic probe designs have deployed focusing optics on the ends of each waveguide, in order to optimize source-detector separation. This design is costly as the focusing optic is an expensive portion of the final probe design. Furthermore, the focusing optic on the collection fiber reduces the viewing angle of the fiber, reducing collection efficiency. In some embodiments, a focusing optic is only deployed in an illumination waveguide's optical path. Furthermore, it was thought that the optimal orientation of illumination and detection waveguides would be designed with the distal port of the collection fiber located more distal than the distal port of the illumination fiber. In some embodiments, the illumination waveguide is oriented such that the illumination beam impinges the sample more distally than the collection beam, with both beams center axes being angled between the sample and the distal end of the probe. This orientation can greatly decrease specular reflection (e.g., from a sample or from a sheath) detected by the collection fiber and allows maximal light collection.

In some embodiments, a multimodal probe may be used in conjunction with a multimodal characterization system (e.g., OCT/NIRS characterization system). In some embodiments, a multimodal characterization system may be used for intraluminal characterization (e.g., coronary artery characterization). In some embodiments, a multimodal probe may be a catheter, for example a cardiac catheter that can be used to rapidly characterize lumens (e.g., arteries) of a patient, in a multimodal manner. In some embodiments, a catheter may be air-filled. For example, an interior volume of a sheath of the catheter and/or any volume between the sheath and a bodily lumen may be substantially devoid of any fluid. For example, an air-filled catheter may be constructed to not have any intervening fluid (e.g., blood or saline) disposed in an optical path for the catheter during characterizing of a bodily lumen (e.g., between optics in the probe and the bodily lumen). In some embodiments, optimizations realized may be specific to air-filled catheters (e.g., to reduce specular reflections, e.g, to optimize illumination and collection beam overlaps, e.g., to optimize signal for each optical modality). In some embodiments, a catheter may be fluid filled [e.g., with a flushing fluid (e.g., saline) or blood]. In some embodiments, a probe may be air-filled. For example, an air-filled probe may be constructed to not have any intervening fluid (e.g., blood or saline) disposed in an optical path for the probe during characterizing of a bodily lumen (e.g., between optics in the probe and the bodily lumen).

FIG. 1 illustrates exemplary embodiments of a multimodal characterization system for coronary artery imaging. The multimodal characterization system includes a console 100, a physician monitor 102, a technician monitor 104 and a tray 106. Attached to the system is a catheter interface unit 110 that interfaces with the console via an electro-optical transmission cable 108 and a patient-interfacing catheter 112.

Figure 2:
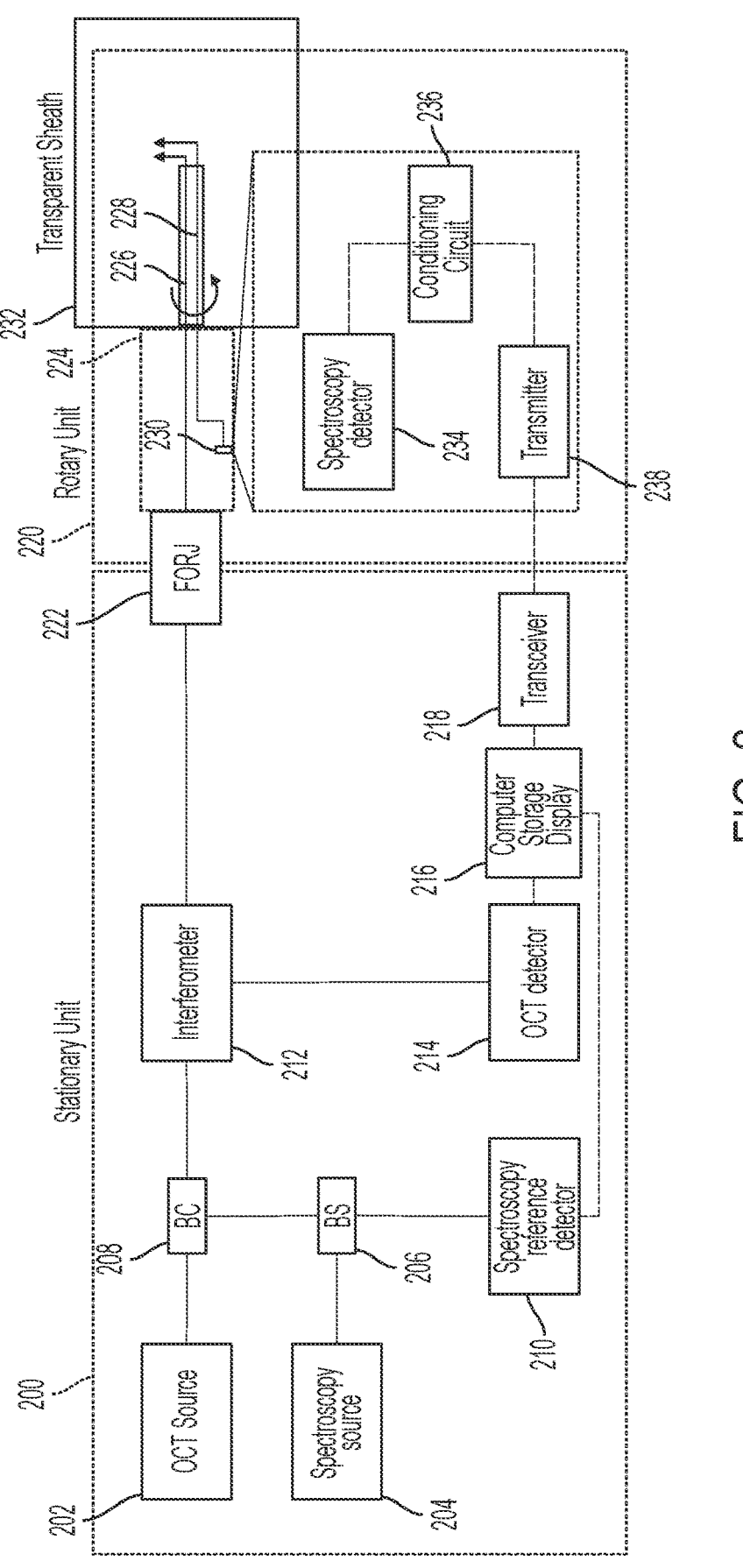
FIG. 2 illustrates a more detailed multimodal imaging system in accordance with illustrative embodiments of the present disclosure.

FIG. 2 illustrates a block diagram for exemplary embodiments of a multimodal characterization system. The multimodal system/apparatus includes a stationary optical unit 200, which may include one or more of an OCT source 202, a spectroscopy source 204, a beam splitter 206 to create a reference channel, a beam combiner (e.g., a WDM) 208 to combine the two sources, a spectroscopy reference detector 210 for detecting a reference measurement, an interferometer 212, an OCT detector 214, a computing device 216 and a transceiver device 218. The stationary optical unit 200 can be optically interfaced with a rotary optical unit 220 via a single channel fiber optic rotary junction (FORJ) 222. The rotary optical unit 220 may include, for example, one or more of a rotary device housing 224, an illumination/collection optical channel (e.g., at least one singlemode fiber in series) 226, a collection optical channel (e.g., at least one multimode fiber in series) 228 and a collection light detector 230. The optical channels extending to the sample may be covered by a transparent sheath 232 for protection and safety considerations. The sheath 232 may remain stationary during operation, for example as in an intravascular characterization catheter. The collection detector device 230 may include a spectroscopy detector 234 as well as a conditioning circuit 236 (e.g., for improving the SNR of the detected signal), and a transmitter 238 (e.g., a slip ring, RF transmitter, or optical transmitter). Transmitter 238 may be a transceiver. In some embodiments, a collection light detector may be located within a stationary optical unit, for example by deploying a dual-channel FORJ or a rotatable combiner. In some embodiments, a collection light detector is disposed within a stationary optical unit in combination with a rotatable combiner disposed within a rotary optical unit. A rotatable combiner may combine electromagnetic radiation (e.g., an illumination optical channel and second waveguide into a third waveguide) for transmission over a double-clad FORJ. Examples of such arrangements are described in International (PCT) Patent Application No. PCT/US2014/013330, filed Jan. 28, 2014, the disclosure of which is hereby incorporated by reference herein in its entirety.

Figure 3:
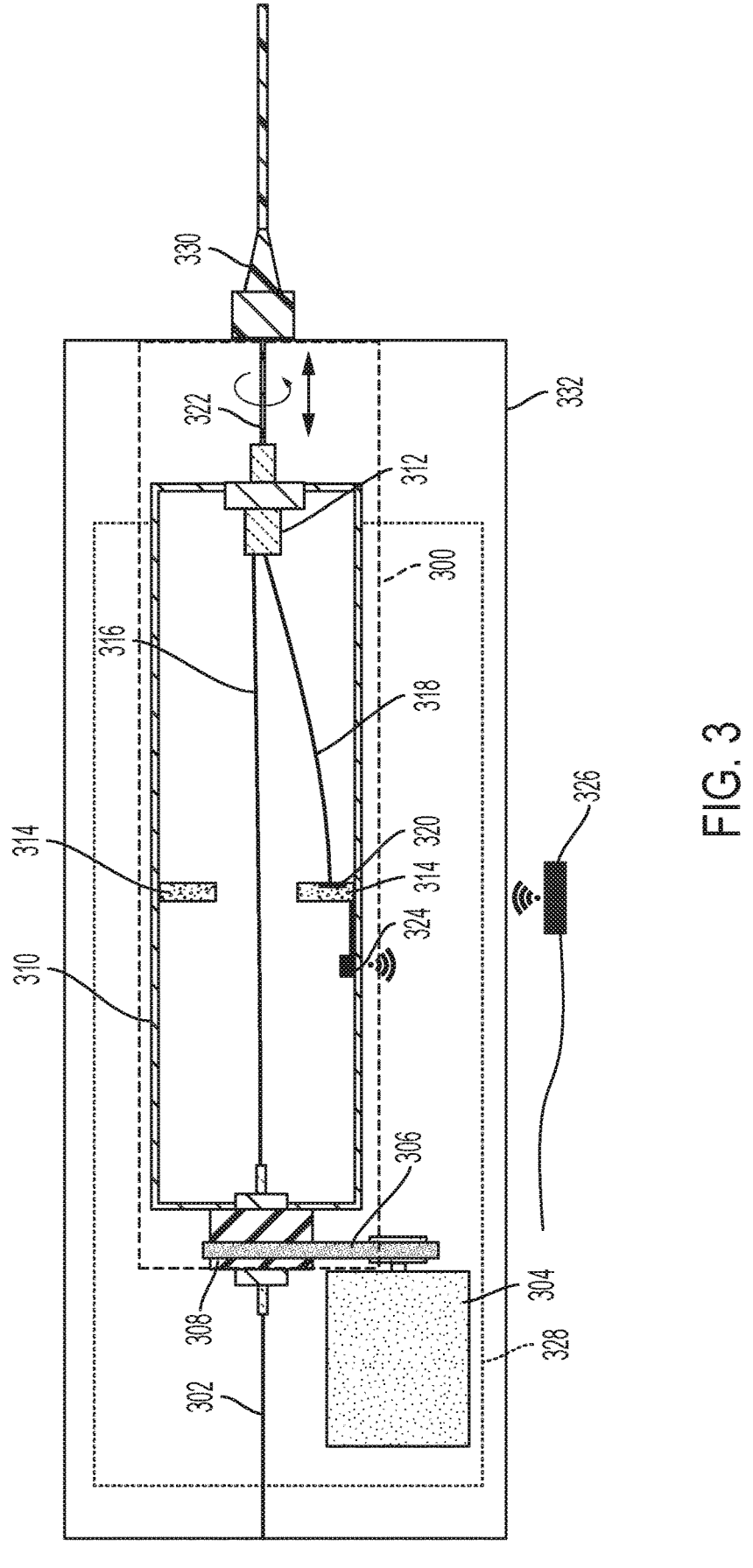
FIG. 3 illustrates an electro-optical rotary junction with stationary and rotating elements for multimodal imaging, in accordance with illustrative embodiments of the present disclosure.

FIG. 3 is a cross section that illustrates exemplary embodiments for a rotary unit that enables high-fidelity, rapid multimodal rotary characterization. A rotary unit 300 may include a FORJ 308 (e.g., portion thereof), a rotary device housing 310 for housing an interconnect 312, a circuit board 314, an illumination optical channel 316, collection optical channel 318 terminating on an optical detection device 320 (e.g., a light detector, optionally including optics) and a multi-optical-channel probe 322 for transmitting and receiving light from a sample. A stationary unit may optically interface with a rotary unit 300 via a stationary optical fiber 302 interfaced with the FORJ 308. A motor 304 that stays stationary in relation to the rotary unit may be used to drive a drive belt 306 in order to transfer torque to the rotary unit 300. In some embodiments, a direct drive motor may be deployed without a drive belt. Within the rotary device housing 310, connected to the circuit board 314, there may exist a wireless transmitter 324 (e.g., a wireless transceiver) to transmit data and/or receive information from the rotary unit to a wireless RF transceiver 326 on the stationary unit. At least a portion of the rotary unit may be attached to a linear translational stage 328, allowing for a forward and backward translation. A probe housing 330 may be designed to house the optical probe 322 and to interface with a stationary housing 332 for the rotary devices, such as to remain rotationally stationary while the inner optical probe 322 is rotated and translated as part of the rotary unit 300. Housings and devices shown may be, for example, round (e.g., circular) or rectangular.

In some embodiments of the present disclosure, a multimodal probe may contain at least two optical waveguides. In some embodiments, the waveguides are disposed within a torque-transfer coil used to rotate the distal probe optics in a circumferential manner (e.g., to image the interior of a bodily lumen (e.g., artery)). In some embodiments, a single waveguide may be used for illumination and detection for a first modality, while either the same waveguide, or another physically separate waveguide may be used for detection of another modality. In some embodiments, there may be any number of waveguides disposed within the torque-transfer coil of a probe (e.g., 3 waveguides). In some embodiments multiple waveguides may be used for illumination (e.g., to provide illumination for different modalities), while two or more waveguides may be used for detection (e.g., each for at least one of the modalities). In some embodiments a single waveguide may perform illumination while two or more waveguides are used for detection (e.g., to detect scattered light from different positions or depths). In some embodiments a single waveguide may perform illumination while the same waveguide and another waveguide may detect backscattered light with different modes (e.g., optical modes). In some embodiments a multimode fiber may be used to transmit and/or to receive multimode light (e.g., for reflectance intensity measurements (e.g., wavelength dependent intensity measurements)). In some embodiments a singlemode fiber may be used to transmit and/or to receive light (e.g., for interferometry). In some embodiments, a doubleclad optical fiber may be used to transmit and/or to receive both singlemode and multimode light.

A multimodality probe should have a proximal and distal end, wherein the distal end is in optical connection with the sample. In some embodiments, a distal port of a waveguide (e.g., where light is optically transmitted to the sample) is offset longitudinally, or circumferentially from another waveguide, such as to optimize a source to detector separation distance for diffuse spectroscopy (e.g., NIRS). In some embodiments, a waveguide has a distal focusing optic in its optical path to focus light, such as to optimize resolution of a characterization modality (e.g., OCT). In some embodiments a focusing optic is a ball lens (e.g., fused to the waveguide at the time of manufacture). In some embodiments, a focusing optic is a gradient index (GRIN) lens (e.g., a GRIN fiber). In some embodiments, a focusing optic is physically connected with a waveguide (e.g., spliced or fused). In some embodiments, a focusing optic is part of an injection molded piece or a 3D printed piece or a machined piece. In some embodiments, a focusing optic is a curved surface (e.g., a curved reflector). In some embodiments a focusing optic may be a metalens. In some embodiments, an aberration correction optic is disposed in a waveguide's optical path. In some embodiments, a focusing optic is shaped (e.g., formed) to correct aberrations. In some embodiments, the focusing optic is part of a larger unit, physically connected with other optics or components (e.g., beam redirectors).

A probe is generally inserted into a lumen and is rotated along its axis to characterize the inner wall of a lumen, approximately parallel with the probe. Therefore, in some embodiments, a waveguide within a probe has a beam redirector (e.g., a mirror) in its optical path, to point the beam towards the lumen. In some embodiments, the beam is redirected approximately perpendicular to the waveguide (e.g., 90 degrees). In some embodiments, a beam redirector may redirect the beam anywhere between 90 degrees and 45 degrees (e.g., 75 degrees) from the axis of the probe (e.g., to reduce specular reflection). In some embodiments, a beam redirection may be accomplished by total internal reflection (e.g., an angled glass surface in air). In some embodiments, a beam redirector is an angled waveguide (e.g., an angle polished waveguide, e.g., an angle polished fiber optic). In some embodiments, a beam redirector is a reflective surface (e.g., a mirror). In some embodiments, a collection waveguide has no distal focusing optics and only a beam redi-
rector, such as to maximize collected light for a character-
ization modality (e.g., Fluorescence). In some embodiments,
the source to detector offset between an illumination wave-
guide and a collection waveguide is enough to optimize the
collection of diffusely reflected light (e.g., relative to specu-
larly reflected light). In some embodiments, a collection
waveguide is positioned longitudinally offset form an illu-
mination waveguide.

In some embodiments, an illumination beam and a col-
lection beam impinge on the sample in the same circumfer-
ential direction (e.g., the center of the beam may overlap
circumferentially). In some embodiments, a first beam may
be directed in a first circumferential direction while another
waveguide's beam may be directed in another circumferen-
tial direction. (e.g., while being directed at the same longi-
tudinal position). Offsetting two waveguides beam either
circumferentially, or longitudinally, helps to control a source
to detector separation, important for optimizing diffuse light
collection (e.g., for diffuse reflectance spectroscopy (DRS)).
In some embodiments, waveguides may be positioned cen-
tral or eccentric to the center of the probe, while still
disposed within a torque-transferring coil. In some embodi-
ments, two waveguides may be located within a torque coil,
where a first waveguide is positioned "in-front" of a second
waveguide, relative to the "viewing" direction of the second
waveguide's beam (e.g., where the second waveguide is
offset more distal to the first waveguide). In some embodi-
ments, waveguides may be positioned in a side-by-side
orientation viewing the sample at the same circumferential
angle. In some embodiments, a first waveguide may be used
to transmit light at a first position on the lumen, while a
second waveguide may detect light at a second position and
a third waveguide may detect light at a third position (e.g.,
in order to measure depth dependent attributes of a sample).
In some embodiments, any combination of multiple wave-
guides may be disposed with beams located, or directed,
towards different locations on the lumen wall (e.g., to
measure various sample depths or positions). In some
embodiments, the beam divergence of a waveguide (e.g.,
multiple waveguides) can be engineered (e.g., by controlling
the numerical aperture of a waveguide) to increase or
decrease the overlap of beams from each waveguide within
a probe. In some embodiments, the angle of incidence of a
beam for a given waveguide (e.g., for multiple waveguides)
can be engineered (e.g., by adjusting the polishing angle of
a waveguide at a glass to air interface) to increase or
decrease the overlap of beams from each waveguide within
a probe. In some embodiments, a distal aperture may be
disposed (e.g., on a protective encasement) to influence the
profile illumination. In some embodiments, a distal aperture
may be disposed to influence detection (e.g., to reduce
specular reflections, e.g., to further separate illumination &
detection areas).

Figure 4:
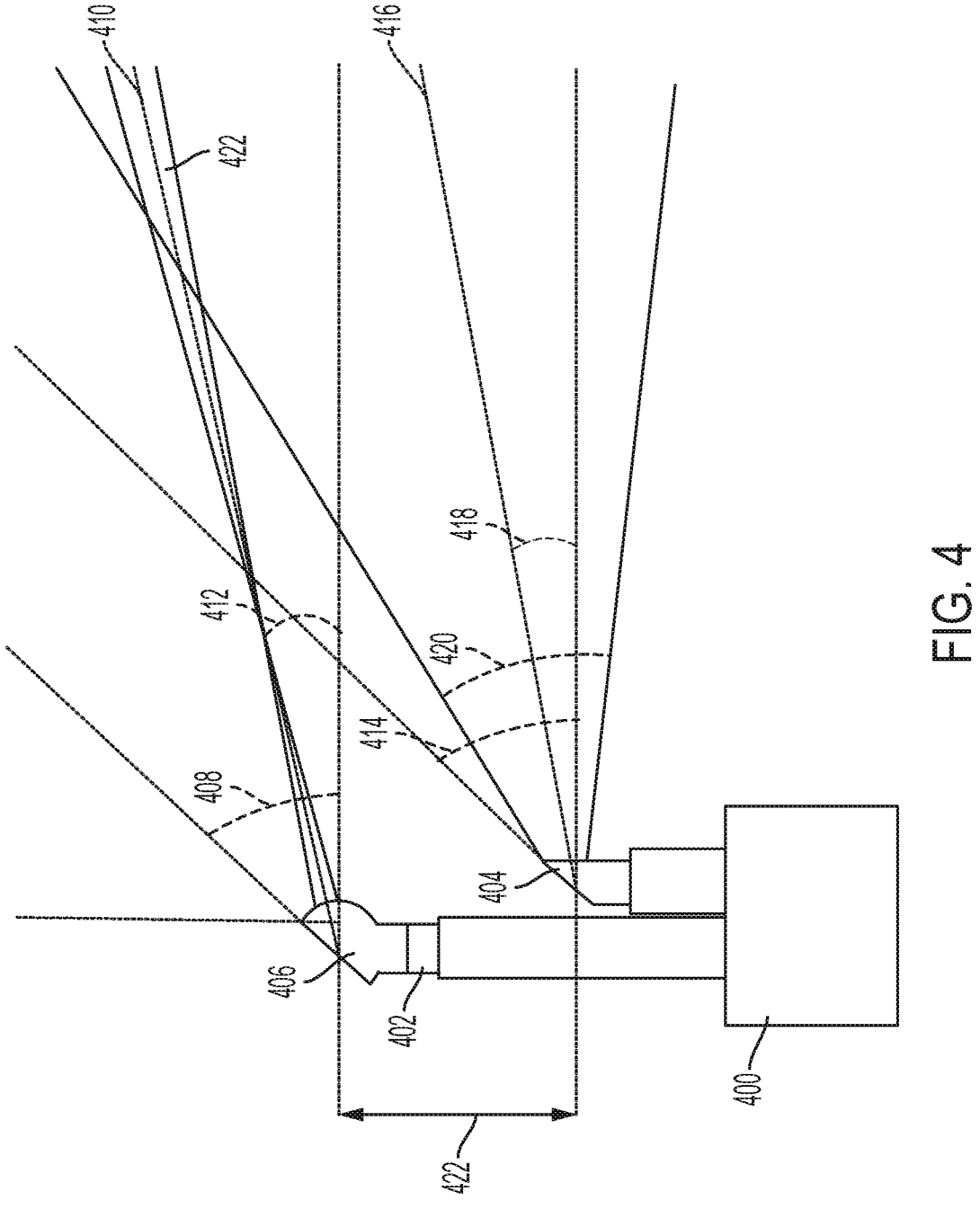
FIG. 4 illustrates a multimodal imaging probe with a focusing ball lens and an angle polished reflective surface terminating one waveguide and an angle polished reflective surface terminating another waveguides, in accordance with illustrative embodiments of the present disclosure.

FIG. 4 is a cross section of a multimodal probe in
accordance with exemplary embodiments of the present
disclosure. Housed in a torque-transferring coil 400, are two
optical waveguides: a first waveguide 402 that transmits and
detects a first modality and a second waveguide 404 that
detects a second modality. The first waveguide is fused to a
ball lens focusing optic 406 to provide a focusing power and
is polished at a controlled angle 408 to optimize the beam
center-axis position 410 and beam center axis angle from the
longitudinal axis (e.g., normal to the longitudinal axis) 412
of the probe. The focusing power of the first waveguide's
beam may be further engineered and optimized by altering
the polishing curvature of the angle polished surface, or by altering ball lens's curvature (e.g., in either the longitudinal
and/or circumferential direction). The second waveguide has
no focusing optic, but is also polished at a controlled angle
414 to optimize the beam center-axis position 416 and beam
center axis angle from the longitudinal axis (e.g., normal to
the longitudinal axis) 418 of the probe. The second wave-
guides acceptance angle 420 may be further engineered and
optimized by altering the numerical aperture of the fiber, or
by altering the curvature of the angle polish. The distance
422 from the distal port of the first waveguide and the distal
port of the second waveguide may be engineering or opti-
mized.

Figures 5A, 5B, 5C, 5D, 5E:
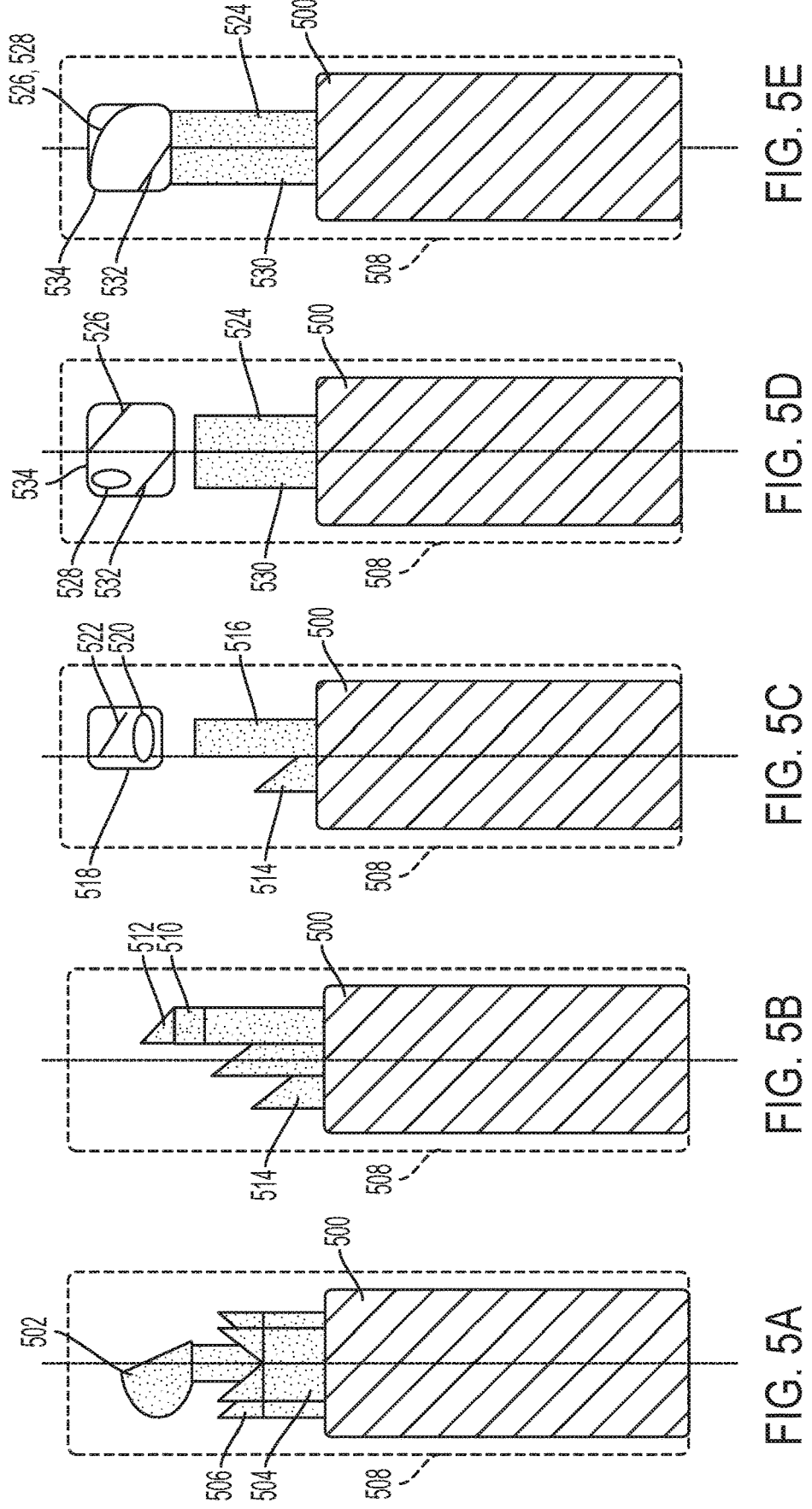
FIG. 5A illustrates a multimodal imaging probe with a focusing ball lens and an angle polished reflective surface terminating one waveguide and an angle polished reflective surface terminating several other waveguides, in accordance with illustrative embodiments of the present disclosure.
FIG. 5B illustrates a multimodal imaging probe a focusing grin lens and an angle polished reflective surface terminating one waveguide and an angle polished reflective surface terminating another waveguide, in accordance with illustrative embodiments of the present disclosure.
FIG. 5C illustrates a multimodal imaging probe with a physically disconnected unit comprising a reflective surface and focusing unit deployed in the optical path of one waveguide and an angle polished reflective surface terminating another waveguide, in accordance with illustrative embodiments of the present disclosure.
FIG. 5D illustrates a multimodal imaging probe with a physically disconnected unit comprising a reflective surface and focusing unit deployed in the optical path of one waveguide as well as a reflective surface for another waveguide, in accordance with illustrative embodiments of the present disclosure.
FIG. 5E illustrates a multimodal imaging probe with a physically disconnected unit comprising a curved reflective surface for both reflecting and focusing in the optical path of one waveguide as well as a reflective surface for another waveguide, in accordance with illustrative embodiments of the present disclosure.

FIG. 5A is a cross section of a multimodal probe in
accordance with exemplary embodiments of the present
disclosure. Housed in a torque-transferring coil 500, are
multiple optical waveguides: a first waveguide 510 with a
fused ball lens focusing optic that transmits and detects a
first modality and a group of a plurality of waveguides 504
for detection of at least a second modality each optically
coupled (e.g., physically coupled) to a prism for beam
redirection 506. The probe is encased by a protective sheath
508, transparent to the modalities.

FIG. 5B is a cross section of a multimodal probe in
accordance with exemplary embodiments of the present
disclosure. Housed in a torque-transferring coil 500, are
multiple optical waveguides: a first waveguide 510 with an
angled optic 512 (e.g., cleaved or polished) that transmits
and detects a first modality and group of collection wave-
guides 514 for detection (e.g., of a second modality) which
have been angle cleaved or polished for beam redirection
506. The collection waveguides are offset longitudinally and
can be optimized for various source to detector separations.
The probe is encased by a protective sheath 508, transparent
to the modalities.

FIG. 5C is a cross section of a multimodal probe in
accordance with exemplary embodiments of the present
disclosure. Housed in a torque-transferring coil 500, are
multiple optical waveguides. A first waveguide 516 is in
optical communication with a first focusing optic (e.g., a
lens) 520 and a second beam redirector 522 (e.g., a mirror,
dielectric mirror), the focusing optic and the beam redirector
located on a substrate 518, deployed in conjunction to
transmit and detect at least a first modality. A second
waveguide 514 for transmission of at least a second modal-
ity which has been angle cleaved or polished for beam
redirection. The probe is encased by a protective sheath 508,
transparent to the modalities.

FIG. 5D is a cross section of a multimodal probe in
accordance with exemplary embodiments of the present
disclosure. Housed in a torque-transferring coil 500, are
multiple optical waveguides. A first waveguide 524 is in
optical communication with a first beam redirector 526 (e.g.,
a mirror, dielectric mirror) and a first focusing optic 528
(e.g., a lens). A second waveguide 530 is in optical com-
munication with a second beam redirector 532, where the
first beam redirector, the second beam redirector and the first
focusing optic are located on a substrate 534. The probe is
encased by a protective sheath 508, transparent to the
modalities.

FIG. 5E is a cross section of a multimodal probe in
accordance with exemplary embodiments of the present
disclosure. Housed in a torque-transferring coil 500, are
multiple optical waveguides. A first waveguide 524 is in
optical communication with a first beam redirector 526 (e.g.,
a 3D printed surface, e.g., molded surface) and a first curved
surface focusing optic 528 (e.g., a 3D printed curved sur-
face, e.g., molded surface) (e.g., an integral printed or molded component). A second waveguide 530 is in optical communication with a second beam redirector 532 (e.g., a 3D printed surface, e.g., molded surface), where the first beam redirector, the second beam redirector and the first focusing optic are located on a substrate 534 (e.g., 3D printed substrate, e.g., a molded substrate). The probe is encased by a protective sheath, transparent to the modalities 508.

Figure 6E:
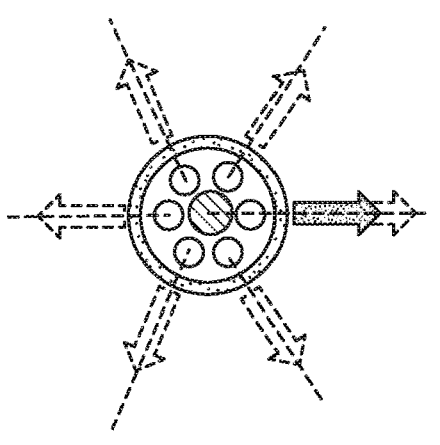
FIG. 6E illustrates a cross-sectional of a multimodal imaging probe with 7 waveguides, where in the illumination beam centerline overlaps with only one of the other waveguide beam centerlines, in accordance with illustrative embodiments of the present disclosure.
Figure 6D:
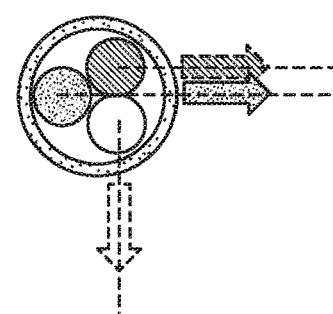
FIG. 6D illustrates a cross-sectional view of a multimodal imaging with three waveguides, two of which have beam centerlines along the same radial direction while one does not, in accordance with illustrative embodiments of the present disclosure.
Figure 6C:
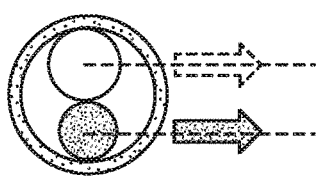
FIG. 6C illustrates a cross-sectional view of a multimodal imaging probe with two waveguides having beam centerlines pointed along the same radial direction but not overlapped, in accordance with illustrative embodiments of the present disclosure.
Figure 6B:
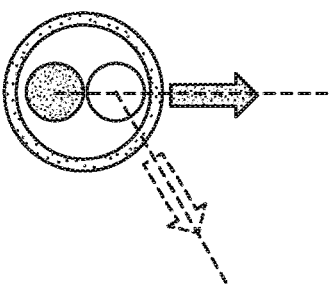
FIG. 6B illustrates a cross-sectional view of a multimodal imaging probe with two waveguides having non-circumferentially overlapped beam centerlines alone the probe axis, in accordance with illustrative embodiments of the present disclosure.
Figure 6A:
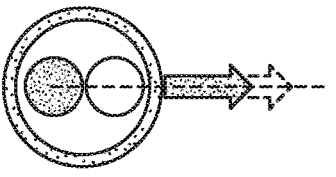
FIG. 6A illustrates a cross-sectional view of a multimodal imaging probe with two waveguides having circumferentially, but not longitudinally, overlapped beam centerlines alone the probe axis, in accordance with illustrative embodiments of the present disclosure.

FIG. 6A is a cross section of a multimodal probe in accordance with exemplary embodiments of the present disclosure where a first waveguide (filled) (e.g., an illumination and detection waveguide) and a second waveguide (empty) (e.g., a detection waveguide) have circumferentially overlapping beam axes. The filled arrow denotes the first waveguides beam axis (e.g., viewing axis) in the circumferential direction, while the empty, dotted perimeter, arrow denotes the second beam axis (e.g., viewing axis) in the circumferential direction. In this orientation, the first waveguide's beam axis is more distal than the second waveguide's beam axis.

FIG. 6B is a cross section of a multimodal probe in accordance with exemplary embodiments of the present disclosure where a first waveguide (filled) (e.g., an illumination and detection waveguide) and a second waveguide (empty) (e.g., a detection waveguide) have circumferentially non-overlapping beam axes. The filled arrow denotes the first waveguides beam axis (e.g., viewing axis) in the circumferential direction, while the empty, dotted perimeter, arrow denotes the second beam axis (e.g., viewing axis) in the circumferential direction. In this orientation, the first waveguide's beam axis is more distal than the second waveguide's beam axis.

FIG. 6C is a cross section of a multimodal probe in accordance with exemplary embodiments of the present disclosure where a first waveguide (filled) (e.g., an illumination and detection waveguide) and a second waveguide (empty) (e.g., a detection waveguide) have circumferentially non-overlapping beam axes. The filled arrow denotes the first waveguides beam axis (e.g., viewing axis) in the circumferential direction, while the empty, dotted perimeter, arrow denotes the second beam axis (e.g., viewing axis) in the circumferential direction. In this orientation, the first waveguide's beam axis is more distal than the second waveguide's beam axis.

FIG. 6D is a cross section of a multimodal probe in accordance with exemplary embodiments of the present disclosure where a first waveguide (filled) (e.g., an illumination and detection waveguide), a second waveguide (empty) (e.g., a detection waveguide) and a third waveguide (line-filled) (e.g., an illumination or detection waveguide), wherein the second and third waveguides have different source to detector distances from the first waveguide (e.g., to discern depth dependent optical properties). The filled arrow denotes the first waveguides beam axis (e.g., viewing axis) in the circumferential direction, while the empty, dotted perimeter, arrow denotes the second beam axis (e.g., viewing axis) in the circumferential direction. In this orientation, the first waveguide's beam axis is more distal than the second waveguide's beam axis.

FIG. 6E is a cross section of a multimodal probe in accordance with exemplary embodiments of the present disclosure where a first waveguide (filled) (e.g., an illumination and detection waveguide) and a group of secondary waveguides (empty) having circumferentially non-overlapping beam axes. The group of secondary waveguides are positioned around the first waveguide, within the torque-transferring coil. The source to detector distance can be controlled between each of the secondary waveguides and the first waveguide to view different areas (e.g., to discern depth dependent optical properties). The filled arrow denotes the first waveguide's beam axis (e.g., viewing axis) in the circumferential direction, while the empty, dotted perimeter, arrows denotes the beam axis (e.g., viewing axis) in the circumferential direction for each of the detection waveguides. In this orientation, the first waveguide's beam axis is more distal than the second waveguide's beam axis.

Figure 7A:
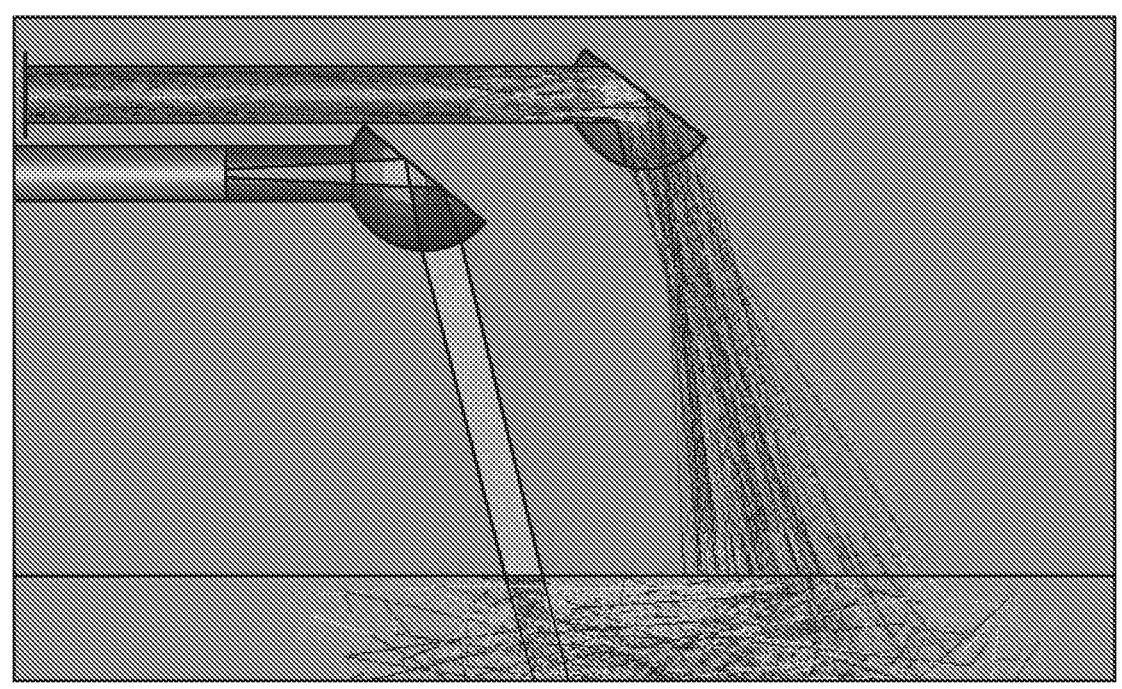
FIGS. 7A-7B illustrate a ray-tracing software simulation of light propagation for a previous probe design, as well as a probe design in accordance with illustrative embodiments of the present disclosure.
Figure 7B:
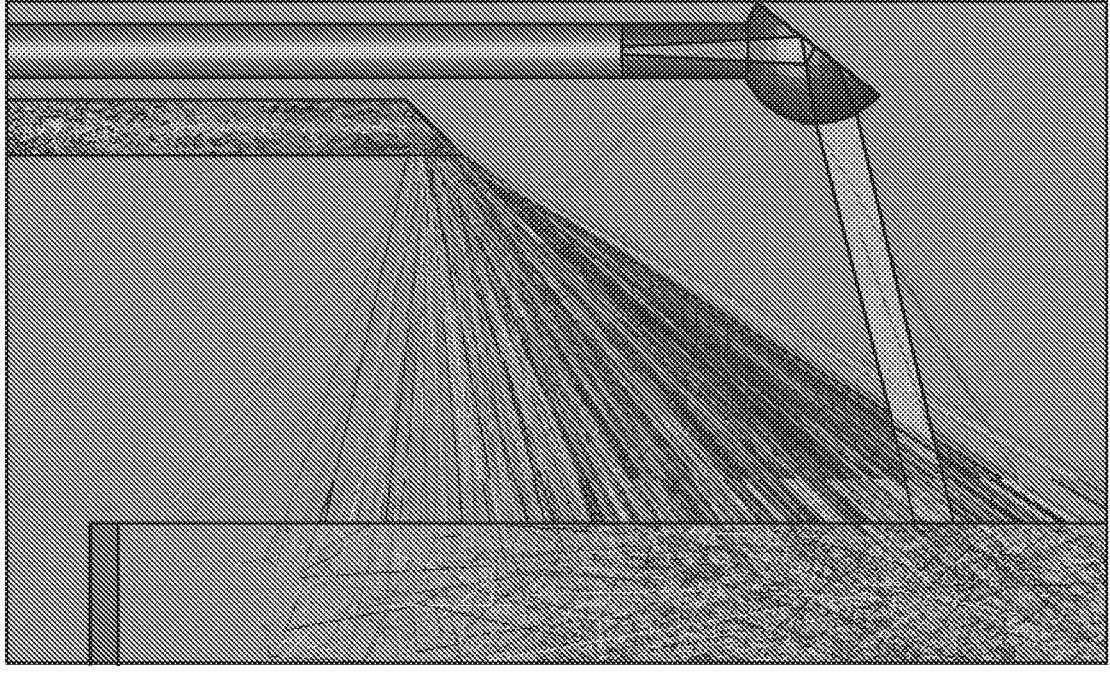

FIG. 7A illustrates a ray-tracing software simulation of light propagation for a previous probe design. FIG. 7B illustrates a probe design in accordance with illustrative embodiments of the present disclosure.

Figures 8A, 8B, 8C, 8D:
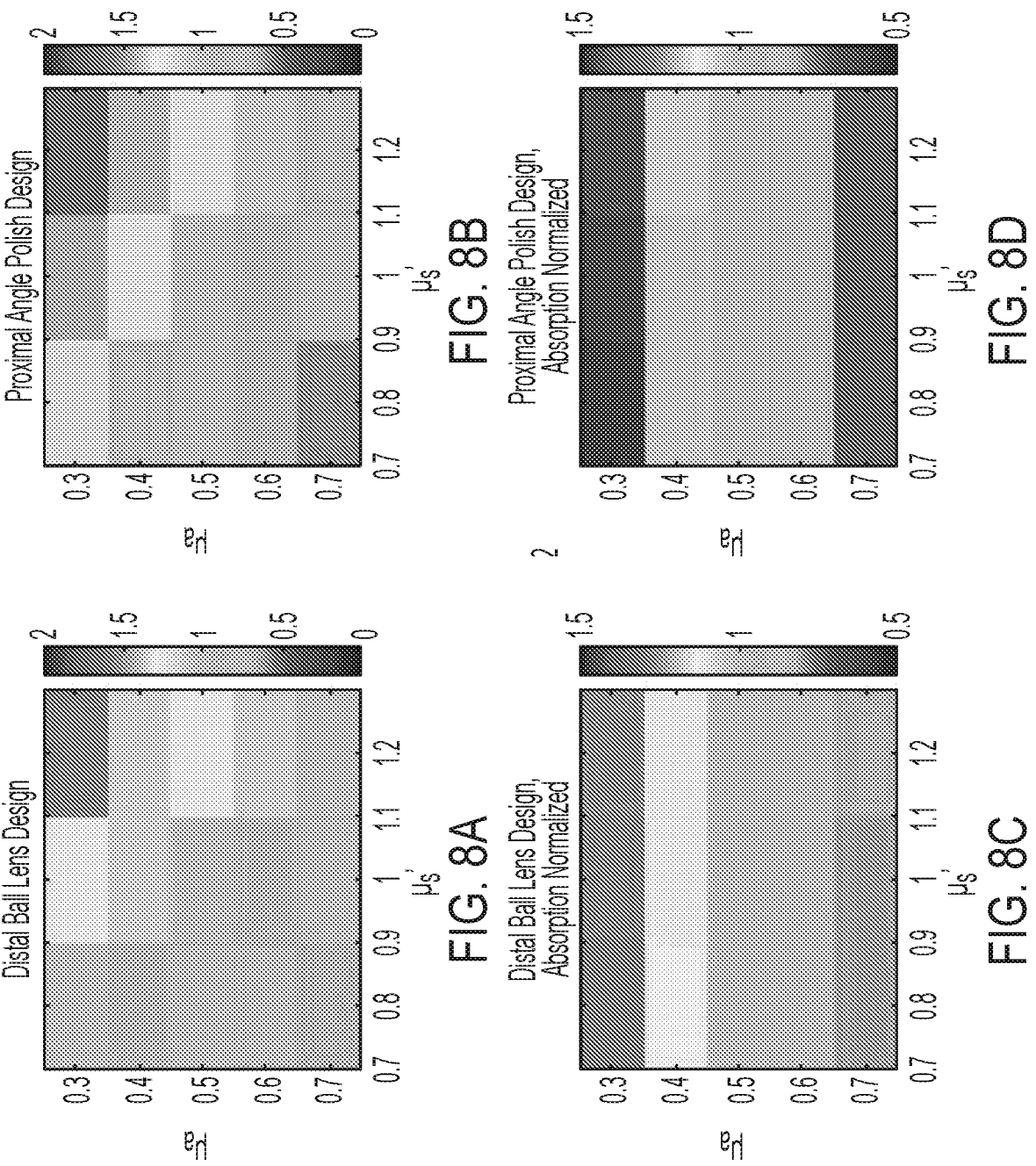
FIGS. 8A-8D illustrate a Monte Carlo simulation for photon propagation to assess the normalized absorption and scattering sensitivity for a previous probe design, as well as a probe design in accordance with illustrative embodiments of the present disclosure.

FIGS. 8A-8D illustrate a Monte Carlo simulation for photon propagation to assess the normalized absorption and scattering sensitivity for previous probe designs, as well as a probe design in accordance with illustrative embodiments of the present disclosure. FIGS. 8A-8B exhibit that for a range of optical properties (absorption and scattering) relevant to biological tissues, both designs may achieve similar performance in sensitivity. FIGS. 8C-8D exhibit that a design without a focusing optic on a detection fiber, relative to a design with a focusing optic on the detection fiber, achieves better relative sensitivity to absorption, when scattering is normalized. Total light collection as well as absorption sensitivity are important to optimize for a spectroscopy device. As shown, the design within this illustrative embodiment of the present disclosure increases the detectable light as well as the sensitivity to the absorption from the sample.

In some embodiments, a protective encasement (e.g., a metal can) is placed near the distal end of the probe (e.g., to protect distal optics or waveguides). In some embodiments, the distal optics of the probe are positioned such as to allow light transmission through a window within the protective encasement (e.g., through the protective encasement). In some embodiments, the protective encasement contains a radiopaque substance (e.g., a radiopaque can). In some embodiments, a radiopaque marker is positioned on the can (e.g., near the distal end of the can).

It is contemplated that systems, devices, methods, and processes of the disclosure encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems according to certain embodiments of the present disclosure that consist essentially of, or consist of, the recited components, and that there are processes and methods according to certain embodiments of the present disclosure that consist essentially of, or consist of, the recited processing steps.

It should be understood that the order of steps or order for performing certain action is immaterial so long as operability is not lost. Moreover, two or more steps or actions may be conducted simultaneously. As is understood by those skilled in the art, the terms "over", "under", "above", "below", "beneath", and "on" are relative terms and can be interchanged in reference to different orientations of the layers, elements, and substrates included in the present disclosure. For example, a first layer on a second layer, in some embodiments means a first layer directly on and in contact with a second layer. In other embodiments, a first layer on a second layer can include another layer there between.

Certain embodiments of the present disclosure were described above. It is, however, expressly noted that the present disclosure is not limited to those embodiments, but rather the intention is that additions and modifications to what was expressly described in the present disclosure are also included within the scope of the disclosure. Moreover, it is to be understood that the features of the various embodiments described in the present disclosure were not mutually exclusive and can exist in various combinations and permutations, even if such combinations or permutations were not made express, without departing from the spirit and scope of the disclosure. The disclosure has been described in detail with particular reference to certain embodiments thereof, but it will be understood that variations and modifications can be effected within the spirit and scope of the claimed invention.

What is claimed is:

1. A probe for characterizing bodily lumens, comprising:
a first waveguide positioned within the probe that transmits and detects a signal from a first characterization modality, the first waveguide comprising a first beam redirector and a focusing optic disposed in an optical path of the first waveguide such that a first beam transmitted by the first waveguide can be focused towards a wall of a lumen; and a second waveguide positioned within the probe that detects a signal from a second characterization modality, the second waveguide having no focusing optic and positioned proximally of the first waveguide.

2. The probe of claim 1, wherein the first waveguide is constructed to detect signal for an interferometric imaging modality.

3. The probe of claim 1, wherein the first and second waveguides are disposed within a torque transfer coil.

4. The probe of claim 1, wherein the first beam redirector and the focusing optic are physically connected with the first waveguide.

5. The probe of claim 1, wherein the first beam redirector is an angled fiber optic.

6. The probe of claim 1, wherein the focusing optic is a ball lens.

7. The probe of claim 1, wherein the focusing optic is a gradient index lens.

8. The probe of claim 1, wherein the first beam redirector and the focusing optic are each a curved mirror surface.

9. The probe of claim 1, further comprising a spectroscopic modality subsystem optically connected to the second waveguide to detect light received through the second waveguide.

10. The probe of claim 1, wherein the second waveguide is optically connected to a light source.

11. The probe of claim 1, comprising a characterization modality subsystem optically connected to the first waveguide such that a reflectance intensity is detected by the first waveguide.

12. The probe of claim 1, comprising an interferometric modality subsystem optically connected to the first waveguide.

13. The probe of claim 1, comprising an intensity modality subsystem optically connected to the second waveguide.

14. The probe of claim 1, wherein the probe is in optical communication with a rotatable combiner.

* * * * *